(12) United States Patent
Afriat

(10) Patent No.: US 7,351,263 B2
(45) Date of Patent: Apr. 1, 2008

(54) COMPLETE KNEE PROSTHESIS

(76) Inventor: Jacques Afriat, 23 Rue de l'Aigle, Narbonne (FR) F-11100

( * ) Notice: Subject to any disclaimer, the term of this patent is extended or adjusted under 35 U.S.C. 154(b) by 635 days.

(21) Appl. No.: 10/504,633

(22) PCT Filed: Feb. 13, 2003

(86) PCT No.: PCT/FR03/00466

§ 371 (c)(1),
(2), (4) Date: Aug. 12, 2004

(87) PCT Pub. No.: WO03/068109

PCT Pub. Date: Aug. 21, 2003

(65) Prior Publication Data

US 2005/0154472 A1   Jul. 14, 2005

(30) Foreign Application Priority Data

Feb. 14, 2002   (FR) .................................. 02 01862

(51) Int. Cl.
*A61F 2/38* (2006.01)
(52) U.S. Cl. ................................ 623/20.27; 623/20.28
(58) Field of Classification Search ............. 623/20.14, 623/20.15, 20.16, 20.17, 20.18, 20.19, 20.2, 623/20.21, 20.22, 20.23, 20.24, 20.25, 20.26, 623/20.27, 20.28, 20.29, 20.3, 20.31, 20.32, 623/20.33, 20.34, 20.35, 20.36
See application file for complete search history.

(56) References Cited

U.S. PATENT DOCUMENTS

| 4,209,861 | A | * | 7/1980 | Walker et al. ........... 623/20.27 |
| 5,011,496 | A | | 4/1991 | Forte et al. |
| 5,370,699 | A | * | 12/1994 | Hood et al. ............... 623/20.28 |
| 6,039,764 | A | * | 3/2000 | Pottenger et al. ......... 623/20.32 |
| 6,123,729 | A | * | 9/2000 | Insall et al. ............... 623/20.31 |
| 6,203,576 | B1 | * | 3/2001 | Afriat et al. .............. 623/20.27 |
| 6,264,697 | B1 | * | 7/2001 | Walker .................... 623/20.27 |
| 6,325,828 | B1 | * | 12/2001 | Dennis et al. ............ 623/20.14 |
| 6,402,786 | B1 | * | 6/2002 | Insall et al. ............... 623/20.35 |
| 6,406,497 | B2 | * | 6/2002 | Takei ....................... 623/20.31 |
| 6,582,469 | B1 | * | 6/2003 | Tornier .................... 623/20.27 |
| 6,699,291 | B1 | * | 3/2004 | Augoyard et al. ........ 623/20.27 |
| 6,770,097 | B2 | * | 8/2004 | Leclercq .................. 623/20.15 |

FOREIGN PATENT DOCUMENTS

| EP | 0 567 705 | 11/1993 |
| FR | 2 805 456 | 8/2001 |

* cited by examiner

*Primary Examiner*—Thomas J Sweet
(74) *Attorney, Agent, or Firm*—Young & Thompson

(57) ABSTRACT

A prosthesis whose condyles (3) have a spiral form, viewed in the saggital plane and the femoral element (1) has a medial lobe (6) with a curved surface. The medial plateau (2) has glenoid cavities (2b) for the condyles (3) and a medial prominence (5) which forms a posterior support surface (5a) against which the lobe (6) is supported in the course of movement of the joint. The glenoid cavities (2b) on the medial plateau (2) and the condyles (3) are congruent in extension and in the first part of the flexion movement of the joint. The posterior sections of the condyles (3) and the medial lobe (6) inscribe circles with the same centres and the medial lobe (6) contacts against the posterior support surface (5a) at the end of the first part of movement and then rests against the posterior support surface (5a) to perform a "roll-back".

3 Claims, 3 Drawing Sheets

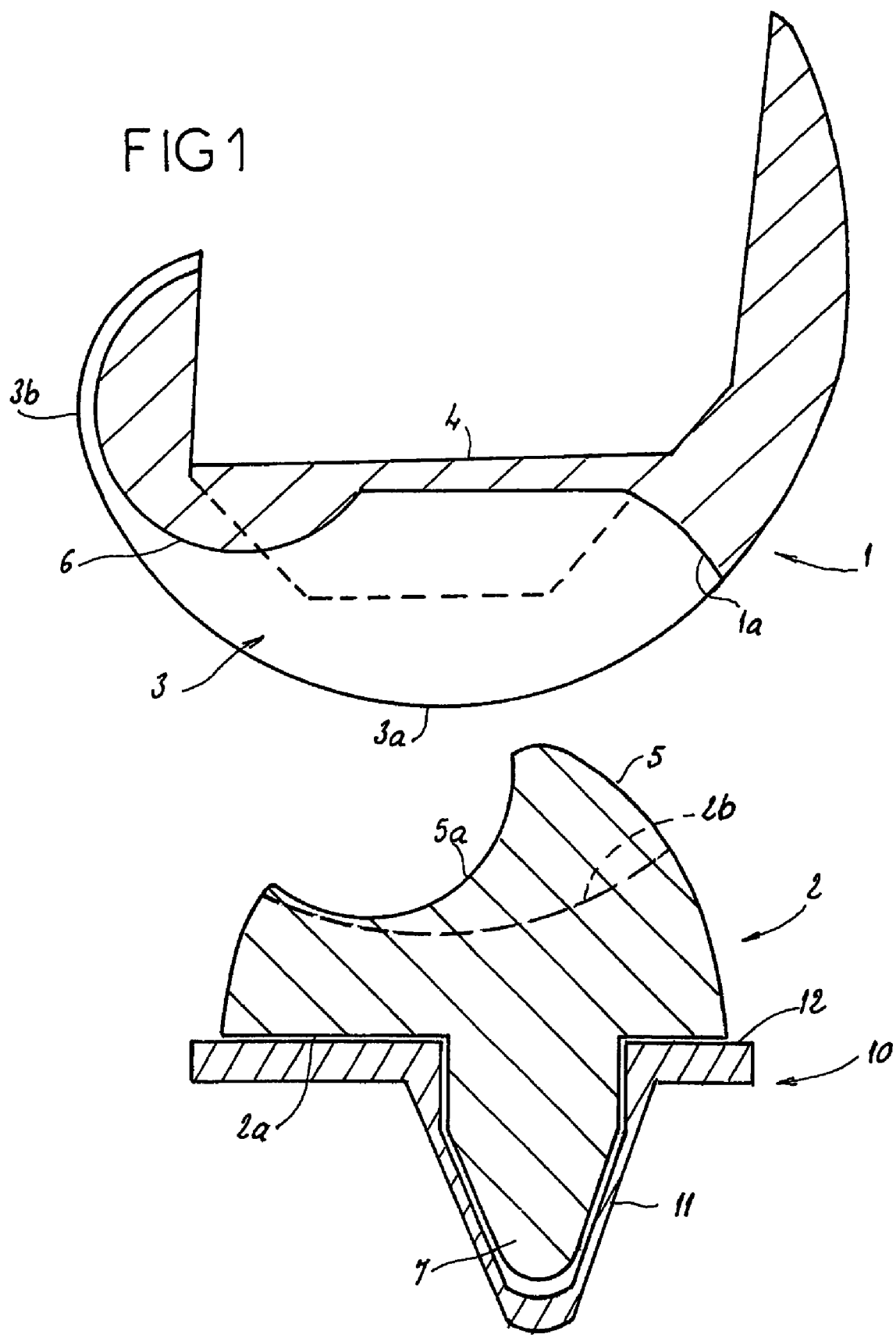

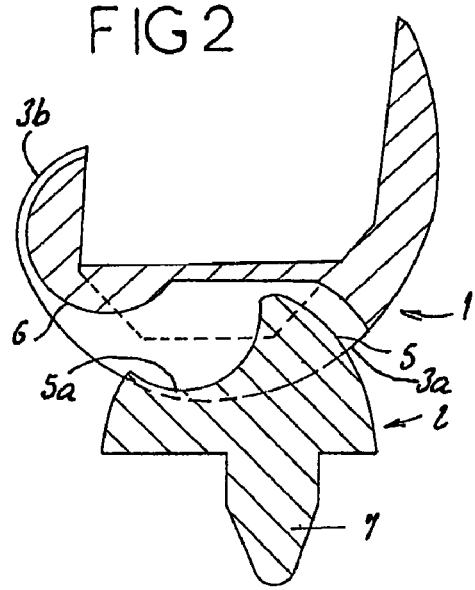
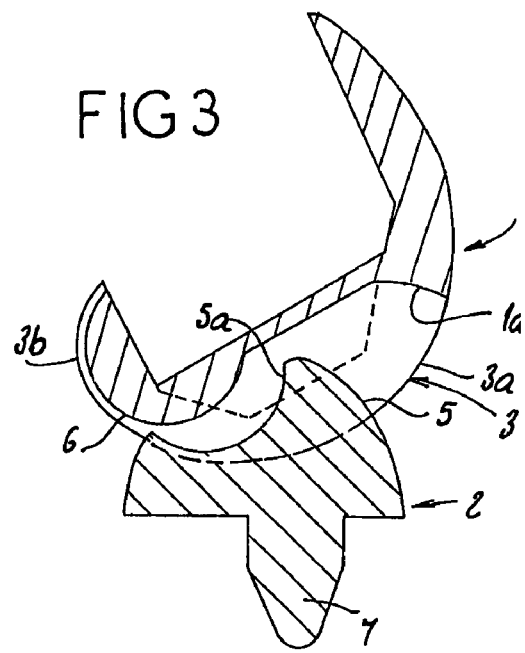
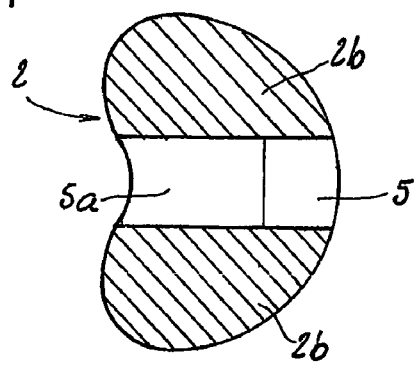

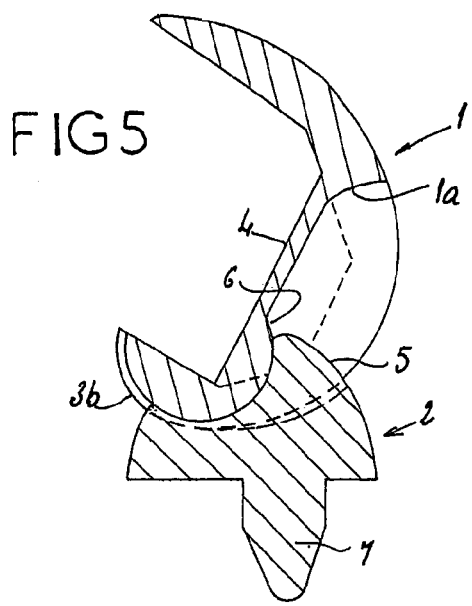
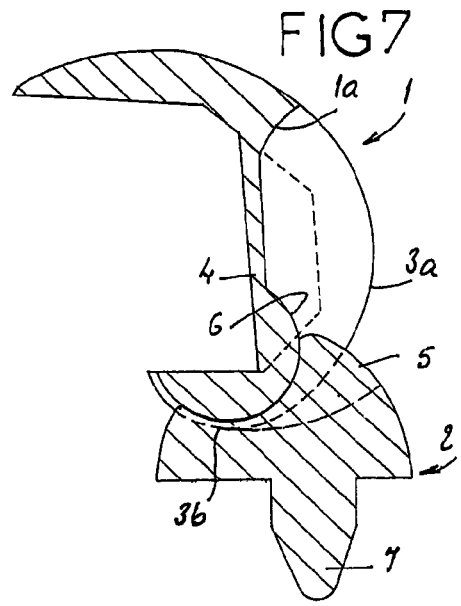
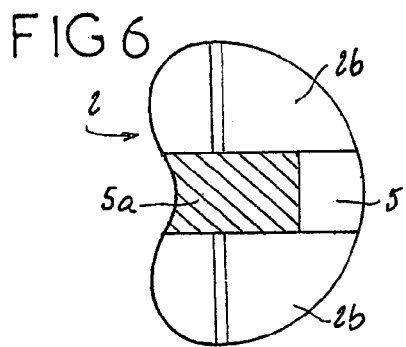
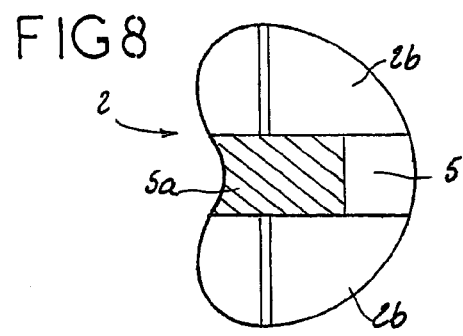
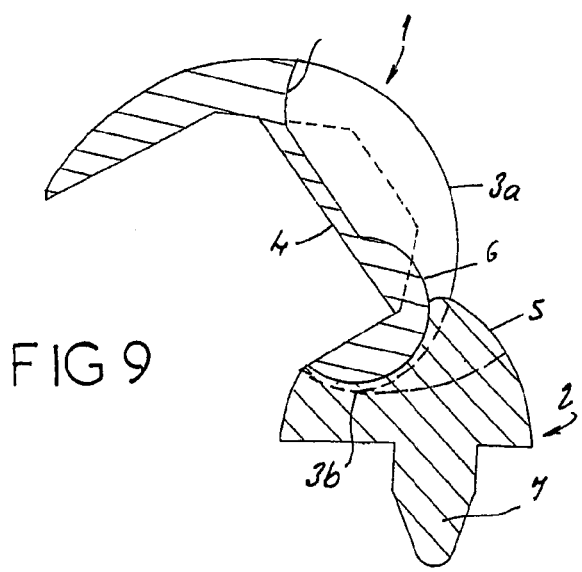
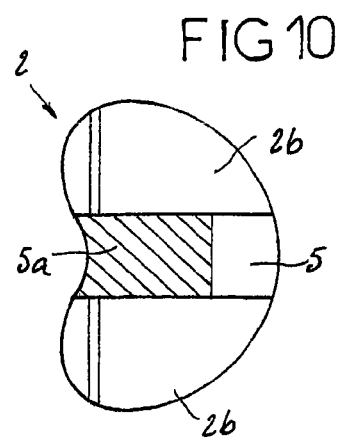

COMPLETE KNEE PROSTHESIS

BACKGROUND OF THE INVENTION

The present invention relates to complete knee prosthesis. Such prosthesis comprises, as it is well known, a femoral element reproducing the femoral condyles, a tibial seat forming an upper support plate and a medial plateau made of a material promoting a slipping movement, notably of high density polyethylene. This medial plateau has a lower face intended for resting against the upper support plate of the tibial seat and glenoid cavities receiving the condyles of the femoral element.

In a complete knee prosthesis, it is advisable that the prosthetic condyles reproduce globally the form of the natural condyles of the knee joint, to obtain good reproduction of the movement of this joint and of an adequate ligamental tension. These prosthetic condyles must therefore have, as seen in the sagittal plane, a spiral form corresponding substantially to that of the natural condyles, i.e. with gradual reduction of their radii towards the posterior sectors.

There results from these reduced radii that the contact surface between the condyles and the medial plateau varies with the flexion movement or the extension of the joint.

Certain prostheses promote the congruence in extension, i.e. between 0 and 40° to 60° approx. in flexion. In such a case, the contact of the prosthetic condyles with the medial plateau, beyond these angles of flexion, becomes linear or even punctual, and non surface-related, which enables the femur to move forward with respect to the tibia, according to a so-called "posterior drawer" movement. This movement is contrary to the physiologic recall movement of the femur with respect to the tibia during the so-called "roll-back" flexion.

It is advisable to reproduce this "roll-back" movement on a knee prosthesis. Indeed, this movement enables to increase the extension force of the quadriceps, while increasing the lever arm thereof. Moreover, this movement enables to delay the moment when the femur abuts against the medial plateau at the end of the flexion and to reduce the camming effect of the soft portions in this very position, which increases the amplitude of movement of the joint and limits the stresses on the bony anchoring interfaces of the femoral element and of the tibial seat.

To solve the problem of so-called "posterior drawer" movement, it is known to adjoin to a knee prosthesis a "postero-stabilisation" system, which consists of a stop between a bar or a lobe provided on the femoral element, between both condyles, and a medial prominence of the medial plateau. This system limits the forward movement of the femur with respect to the tibia, but the contact surface between the femur and the medial element is necessarily linear or punctual in flexion. This limited contact surface is a source of wear for the medial plateau and is therefore detrimental to the perennity thereof.

Certain prostheses enable surface congruence in extension and flexion: the posterior sagittal condylian radius inscribes a circle, and the medial plateau has glenoid surfaces with corresponding circular profile. In such a case, the surface contact is maintained throughout the flexion, but, taking into account this congruence, the translation movements of the femur with respect to the medial plateau are limited or impossible.

Certain prostheses enable antero-posterior mobility between the medial plateau and the tibial element. In such a case, the movement of the femur with respect to the tibia results not from the form of the contact surfaces but from the action of the muscles and of the ligaments. The "roll-back" movement aforementioned being essentially controlled by the posterior cross ligament, these prostheses impose the conservation of this posterior cross ligament, which is not always possible, requested or advisable.

SUMMARY OF THE INVENTION

The purpose of this present invention is to remedy the shortcomings aforementioned of the extent complete knee prostheses, while supplying a "postero-stabilisation" prosthesis enabling to maintain high congruence between the femoral element and the medial plateau over the whole movement of the joint, while enabling perfectly controlled "roll-back" movement, and without imposing the conservation of the posterior cross ligament.

The prosthesis affected comprises, in a manner known in itself, a femoral element, a tibial seat and a medial plateau as aforementioned, the femoral condyles having, seen in the sagittal plane, a spiral form corresponding substantially to that of the natural condyles, i.e. with gradual reduction of their radii towards posterior sectors, and the medial plateau having a medial prominence which forms a posterior support surface, while the femoral element has a medial lobe with a curved surface, capable of resting against this posterior support surface during the movement of the joint.

According to the invention, the glenoid cavities of the medial plateau and the condyles of the femoral element are formed to be congruent when the prosthesis is in extension and on a first part of the flexion movement of the joint extending between this extension position and the angle of flexion from which the congruence of the condyles with the glenoid surfaces is lost due to the spiral form of the condyles;

the posterior sectors of the condyles and of the medial lobe inscribe circles of same centres;

the medial lobe is formed so as not to contact said posterior support surface during said first part of movement, but to contact said posterior support surface when said flexion angle is reached and then to carry the joint against this posterior support surface over the remainder of the flexion travel, while performing a "roll-back", i.e. a rolling movement of the femoral condyles with respect to the tibial seat in the posterior direction, and said posterior support surface has a curved shape corresponding to that of said medial lobe, so that this lobe rests against this posterior support surface over a wide surface throughout the second part of movement, consecutive to said first part of movement.

The prosthesis according to the invention thus comprises femoral condyles of spiral form having a congruence with the medial plateau on said first part of flexion movement. This form and this congruence enable good reproduction of the movement of the natural joint and good control of the movement of the femur with respect to the tibia and conversely.

At said angle of flexion, the medial lobe contacts said posterior support surface, according to a soft and gradual movement resulting from curved forms complementary to this lobe and to this surface. This soft and gradual contact avoids any shock liable to stress the bony anchorings.

From this flexion angle, the resting of the lobe against said posterior support surface compensates for the loss of congruence of the femoral condyles with the medial plateau, which enables to keep the control of the movement of the femoral element with respect to the tibial seat and conversely; the fact that the posterior sectors of the condyles and of the medial lobe inscribe circles of same centres enables to perform the "roll-back" movement, which enables not only to reproduce the anatomic movement, but also to increase the amplitude of the flexion movement of the joint and not to generate detrimental stresses on the bony anchorings at the end of this flexion movement.

The medial plateau is advantageously mobile with respect to the tibial seat in order to limit the stresses exerted on this plateau on the bony anchorings. Notably, this plateau may be mounted to pivot on the tibial seat by means of a stud included in the medial plateau or the tibial seat, engaged in a corresponding cavity provided respectively in the seat or the medial plateau.

BRIEF DESCRIPTION OF THE DRAWINGS

An embodiment of the prosthesis according to the invention is described below with reference to the appended schematic drawing, wherein:

FIG. 1 is a sagittal view thereof, as a medial antero-posterior sectional view;

FIGS. 2, 3, 5, 7 and 9 are sagittal views, as medial antero-posterior sectional views, of the femoral element and of the medial plateau of this prosthesis, respectively in extension position of the prosthesis and according to 30°, 60°, 90° and 125° flexion angles; and FIGS. 4, 6, 8, 10 are planar views of the medial plateau, showing as hatched lines the contact zones of the femoral element with this medial plateau, respectively in the positions of this femoral element and of the medial plateau shown on FIGS. 2 and 3, 5, 7 and 9.

DESCRIPTION OF THE PREFERRED EMBODIMENTS

FIG. 1 represents a femoral element 1, a medial plateau 2 and a tibial seat 10 of a complete knee prosthesis. The tibial seat 10 shows a medullar keel 11 enabling its anchoring in the tibia, an upper plate 12, intended for receiving the medial plateau 2, and a cylindro-conical cavity provided in the keel 11.

The femoral element 1 has a curved shape liable to surround the distal end of the femur. It shows rounded external faces and internal facets intended for resting against the bone, after adequate resection thereof. For its anchoring to the femur, it may include a medullar rod and/or studs, not represented.

The femoral element 1 forms lateral condyles 3 having, as seen in the sagittal plane, a spiral form corresponding substantially to that of the natural condyles, i.e. with gradual reduction of their radii towards to the posterior sectors. Thus, the medial or antero-medial zone 3a of these condyles 3, which is carrying between 0 and approx. 50° of flexion (cf. FIGS. 2 and 3) shows, as seen in the sagittal plane, substantially curbed shape of a first radius while the posterior sector 3b of the condyles 3 inscribes substantially a circle of a second circle vastly smaller than said first radius.

In the front plane, these condyles 3 have a convex curved shape.

On the anterior part of the femoral element 1, the condyles 3 delineate between themselves an elongated cavity reproducing substantially the anatomic trochlea. At its medial zone, the femoral element 1 includes a medial cage 4, elongated in the antero-posterior direction, which delineates a cavity open downwards. This cavity is liable to receive a prominence 5 of the medial plateau 2, described below.

As appears with reference to FIGS. 1 and 2, the femoral element 1 shows a rounded anterior face 1a which, in hyperextension position of the joint, rests against the rounded anterior face of the prominence 5.

On its posterior part, the femoral element 1 includes a rounded medial lobe 6. As shown on the Figures, the posterior sector of this lobe 6 inscribes a circle of the same centre as the circle inscribed by the posterior sectors 3b of the condyles 3.

The lobe 6 is arranged at a certain distance from said prominence 5 of the plateau 2 in extension position of the prosthesis (cf. FIG. 2) and beneath a flexion angle of 60° (cf. FIG. 3). From this flexion angle of 60° (cf. FIG. 5), this lobe 6 rests against this prominence 5 until the position of total flexion (cf. FIGS. 7 and 9). In the front plane, the lobe 6 has a curved and convex shape.

The medial plateau 2 is made of a material promoting a slipping movement, notably of high density polyethylene. It shows a lower face 2a intended for resting against the upper plate 12 of the tibial seat 10 and glenoid cavities 2b receiving the condyles 3 of the femoral element 1. These glenoid cavities 2b have a curvature corresponding to that of the zones 3a of the condyles 3, with which they are consequently congruent beneath a flexion angle of 60°. In the front plane, they have a curvature which corresponds to that of the condyles 3 in this same plane.

The plate 2 includes a cylindro-conical stud 7 protruding in its face 2a, having a diameter slightly smaller than that of the cavity of the keel 11, which may receive this pivoting stud 7.

As visible on FIGS. 2 and 3, the glenoid surfaces 2b and the condyles 3 are formed in order to be congruent when the prosthesis is in extension as well as on the portion of the flexion movement extending beneath a flexion angle of 60°. The contact of the condyles 3 with the glenoid surfaces 2b extends over zones of substantially same surface area as that of these glenoid surfaces 2b, as shown on FIG. 4.

From the flexion angle of 60° and beyond this angle, there appears gradually a space between the condyles 3 and the surfaces 2b (cf. FIG. 5), resulting from the aforementioned reduction in the radii of the condyles 3. The contact surface between the condyles 3 and the surfaces 2b is thereby reduced gradually to switch from a maximum extend beneath 600 to purely linear contact, as shown on FIG. 6.

The medial prominence 5 forms then a posterior support surface 5a having globally the same curvature as that of the lobe 6, emerging approximately at the quarter of the width of the plateau 2 from the posterior edge of this plateau and having its apex approximately at one third of the width of the plateau 2 from the anterior edge of this plateau. This surface 5a has a concave shape in the front plane, whereof the curvature corresponds to that of the lobe 6 in this plane.

As appears on FIGS. 5 to 10, at a flexion angle of 60°, the lobe 6 contacts the surface 5a according to a soft and gradual movement resulting from curved shapes complementary of this lobe 6 and of this surface 5a. This soft and gradual contact 5 avoids any shock liable to stress the bony anchorings.

From this flexion angle of 60°, the support surface of the lobe 6 against the surface 5a compensates for the loss of congruence of the condyles 3 with the plateau 2, as shown on FIGS. 6, 8 and 10, which enables to keep control over the movement of the femoral element 1 with respect to the tibial seat 10 and conversely; the identical shape of the lobe 6 and of the condyles 3 at the posterior sectors of this lobe 6 and of these condyles 3 enables to perform a "roll-back" movement, i.e. a rolling movement of the condyles 3 with respect to the tibial seat in the posterior direction. This rolling movement enables recall of the linear contact surfaces of the condyles 3 with respect to the plateau 2, over some ten millimetres in the example represented, as shown on FIGS. 6, 8 and 10. This movement enables not only to reproduce the anatomic movement of the joint, but also to increase the amplitude of the flexion movement of the joint and not to generate detrimental stresses on the bony anchorings at the end of this flexion movement.

As appears from the foregoing, the invention provides a complete knee prosthesis with "postero-stabilisation", exhibiting decisive advantages of maintaining high congruence between the femoral element and the medial plateau over the whole movement of the joint, while enabling perfectly controlled "roll-back" and without imposing the conservation of the posterior cross ligament.

It goes without saying that the invention is not limited to the embodiment described here above by way of example but it includes, conversely, all the realisation variations covered by the claims appended below. Notably, the condyles 3 and the plateau 2 may be formed so that the contact of the lobe 6 with the prominence 5 takes place at flexion angles other than 60°, for example 30°, 40° or even 80°; the "roll-back" movement may range, according to the conformation of the lobe 6 and of the prominence 5, from 2 to 20 mm.

The invention claimed is:

1. Complete knee prosthesis, comprising:
    a femoral element (1) with femoral condyles (3) having, seen in the sagittal plane, a spiral form corresponding substantially to a form of natural condyles, with gradual reduction of their radii towards posterior sectors, and comprising a medial lobe (6) with a curved surface;
    a tibial seat forming an upper support plate, and
    a medial plateau (2) intended for resting against said upper support plate of the tibial seat and comprising glenoid cavities (2b) receiving the condyles (3) of the femoral element (1), said medial plateau (2) having a medial prominence (5) which forms a posterior support surface (5a), against which said lobe (6) is capable of resting during the movement of the joint, wherein,
    the glenoid cavities (2b) of the medial plateau (2) and the condyles (3) of the femoral element (1) are formed to be congruent when the prosthesis is in extension and on a first part of the flexion movement of the joint extending between this extension position and the angle of flexion between about 30 to 80° from which the congruence of the condyles (3) with the glenoid surfaces is lost due to the spiral form of the condyles (3),
    the posterior sectors of the condyles (3) and of the medial lobe (6) inscribe circles of same centers,
    the medial lobe (6) is formed so as not to contact said posterior support surface (5a) during said first part of movement, but to contact said posterior support surface (5a) when said flexion angle is reached and then to carry the joint against this posterior support surface (5a) over the remainder of the flexion travel, while performing a rolling movement of the femoral condyles (3) with respect to the tibial seat in the posterior direction, called "roll-back", and
    said posterior support surface (5a) has a curved shape corresponding to the curved shape of said medial lobe (6), so that this lobe rests against this posterior support surface (5a) over a wide surface throughout the second part of movement, consecutive to said first part of movement.

2. Prosthesis according to claim 1, characterised in that the medial plateau (2) is mobile with respect to the tibial seat.

3. Prosthesis according to claim 2, characterised in that the medial plateau (2) is mounted to pivot on the tibial seat by means of a stud included in the medial plateau (2) or the tibial seat, engaged in a corresponding cavity (7) provided respectively in the tibial seat or the medial plateau (2).

* * * * *